United States Patent [19]

Lippitsch et al.

[11] Patent Number: 5,464,587
[45] Date of Patent: Nov. 7, 1995

[54] LUMINESCENCE-OPTICAL INDICATOR FOR DETERMINING THE ACTIVITY OF ALKALI METAL IONS IN A SAMPLE SOLUTION

[75] Inventors: Max Lippitsch; Sonja Draxler; Marco J. Leiner, all of Graz, Austria

[73] Assignee: AVL Medical Instruments AG, Schaffhausen, Switzerland

[21] Appl. No.: 242,974

[22] Filed: May 16, 1994

[30] Foreign Application Priority Data

Jun. 9, 1993 [AT] Austria .................................... 1129/93

[51] Int. Cl.⁶ .................................................. G01N 21/64
[52] U.S. Cl. .................................. 422/82.07; 422/82.08; 436/79; 436/172
[58] Field of Search ............................ 422/82.07, 82.08, 422/82.06, 82.05; 436/74, 79, 172

[56] References Cited

U.S. PATENT DOCUMENTS

| | | | |
|---|---|---|---|
| 4,762,799 | 8/1988 | Seitz et al. | 436/79 |
| 5,030,420 | 7/1991 | Bacon et al. | |
| 5,154,890 | 10/1992 | Mauze et al. | |

FOREIGN PATENT DOCUMENTS

| | | |
|---|---|---|
| 384677 | 12/1987 | Austria . |
| 393035 | 7/1991 | Austria . |
| 0358991 | 3/1990 | European Pat. Off. . |

OTHER PUBLICATIONS

H. He et al., "Fluorescence Based Uptrodes for Alkali Ions Based Ions Based on the Use of Ion Carriers and Lipophilic Acid/Base Indicators" in SPIE, vol. 1368 (1990).
L. R. Sousa et al., "Crown Ether Model systems for the Study of Photoexcited State Response to Geometrically Oriented Perturbers. The Effect of Alkali Metal Ions on Emission form Naphthalene Derivatives" in J. Am. Chem., 99, 307, 1977.
R. A. Bissell et al., "Luminescence and Charge Transfer. Part 2. Aminomethyl Anthracene Derivatives as Fluorescent PET (Photoinduced Electron Transfer) Sensors for Protons" in J. Chem. Soc. Perkin Trans. 2, 1992, 1559–1564, 1992.
I. Aoki et al., "A New Metal Sensory System Based on Intramolecular Fluorescence Quenching on the Ionophoric Calix[4]arene Ring" in J. Chem. Soc. Chem. Commun. 1992, 730–732, 1992.
H. He et al., "Novel Type of Ion–Selective Fluorosensor Based on the Inner Filter Effect: An Optrode for Potassium" in Am. Chem., 65, 123–127, 1993.
M. E. Lippitsch et al., "Fibre–Optic Oxygen Sensor with the Fluorescence Decay Time as the Information Carrier" in Anal. Chimica Acta., 205, 1–6, 1988.
J. R. Lakowicz et al., "Fluorecence Lifetime Imaging of Calcium Using Quin–2" in Cell Calcium, 13, 131–147, 1992.
M. K. Carroll et al., "Fiber–Optic Time–Resolved Fluorescence Sensor for the Simultaneous Determination of $Al^{3+}$ and $Ga^{3+}$ or $In^{3+}$" in Anal. Chem. 61, 1768–1772, 1989.

*Primary Examiner*—Jeffrey R. Snay
*Attorney, Agent, or Firm*—Watson, Cole, Grindle & Watson

[57] ABSTRACT

A luminescence-optical indicator for determining the activity of alkali metals based on decay time includes at least three components that are chemically bound to one another, i.e., a fluorophor, a functional group with which the luminescence decay time of the fluorophor can be influenced, and a ionophor binding the alkali metal ions to be measured in a selective and reversible manner, the effect of the functional group on the decay time of the fluorophor being altered in dependence on the activity of the alkali metal ions.

13 Claims, 1 Drawing Sheet

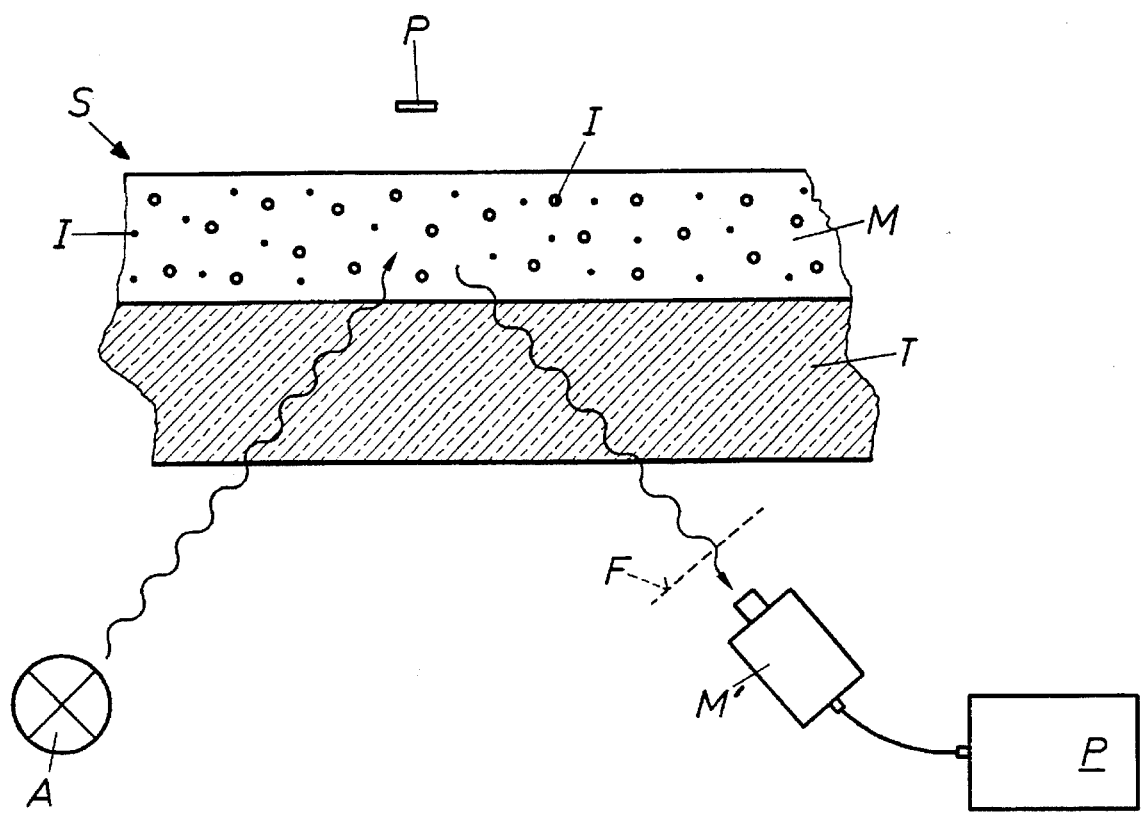

LUMINESCENCE-OPTICAL INDICATOR FOR DETERMINING THE ACTIVITY OF ALKALI METAL IONS IN A SAMPLE SOLUTION

BACKGROUND OF THE INVENTION

The invention relates to a luminescence-optical indicator for determining the activity of alkali metal ions in a sample solution, the solution being at least in indirect contact with the indicator, and a sensor configuration with such an indicator.

Measuring the activity of alkali metal ions is of particular relevance in medical applications. The electrolytic equilibrium in blood, for instance, is essentially determined by sodium and potassium among others, while lithium plays a major role for the cerebral function.

DESCRIPTION OF THE PRIOR ART

Ionic concentrations or activities may be measured in various ways, for example by means of potentiometric methods or optical measurements using so-called optodes.

Potentiometric electrodes have been employed for many years to determine cations in sample solutions. In the course of the measuring process the ion-selective membrane of the electrode is exposed to the liquid sample. On the membrane surface the ion-selective ionophor contained in the membrane reacts with the ion to be determined in the sample solution. In this manner a membrane potential is generated whose size depends on the concentration of the ion present in the sample solution. Although the degree of complex formation is very small, the generated potentials can be reliably determined by such potentiometric methods.

Major disadvantages of ion-selective electrodes are their need for a reference element, poor miniaturizability, sensitivity to electrochemical potentials and electromagnetic interferences, need for individual calibration prior to measurement.

Optodes, on the other hand, do not require a reference element. Optical signals are independent of external potentials and electric currents. All optodes for determining ionic concentrations that are known in the art are based on a measurement of the fluorescence intensity of a fluorophor or the light absorption of a chromophor in dependence of the ionic activity. In view of the fact, however, that optical signals are influenced by the concentration of the indicator, the intensity of the particular light source, and the variability of detector sensitivity, calibration with a suitable calibrating medium is required prior to measurement.

Optodes permit the development of miniaturized measuring elements. This is of special importance in the instance of very small sample volumes, and for the design of catheters for invasive measuring techniques in clinical chemistry and medicine.

In recent times a number of optical sensors have been discussed for measuring ionic concentrations of alkali metals, which are preferably based on a change in the light absorption, or rather, in the fluorescence intensity of a suitable indicator effected by the ions (or, in more general terms, a change in the intensity of the indicator's photoluminescence; for the sake of simplicity, the term of fluorescence will be used in the following paragraphs, which is to include all kinds of photoluminescence, however).

In AT-B 384 677 an optical potassium sensor is disclosed which comprises the potassium-selective valinomycin ionophor and a potential-sensitive fluorophor in a thin polymer membrane. As with the electrodes mentioned above, the binding of potassium ions by the ionophor results in a difference in potential at the interface between membrane and sample solution. The electric potential depending on the concentration of potassium ions will alter the fluorescence intensity of the potential-sensitive fluorophor. The degree of potassium complexing effected by the ionophor is very small in such devices, however. As a consequence, the sensitivity of such devices is low and does not permit a precise quantitative determination of the cationic concentration in the sample.

As is described in EP-A 0 358 991, the above disadvantages may be eliminated by adding a chromophor to the supporting material containing the cation-selective ionophor, which chromophor can transfer another cation to the sample solution if the sample cations to be determined are complexed by the cation-selective ionophor in the membrane. The degree of complexation and the change in the optical signal are considerably larger in this instance than with the configuration described in AT-B 384 677. It is known, however, that the degree to which the optical signal changes will depend not only on the activity of the cation to be determined in the sample solution, but also on the activity of the cation to be transferred from the supporting membrane to the sample solution. It is known from the relevant literature (H. He and O. S. Wolfbeis; SPIE vol 1368, 1990) that the chromophor of EP-A 0 358 991 may be replaced by a fluorophor. For practical purposes, where the cation to be transferred is usually a proton, this implies that the measurement of alkali metal ions by means of such devices also depends on the pH value of the sample.

Sousa and Larson (Journal of the American Chemical Society 99, 307, 1977) describe the intensity change of the intrinsic fluorescence of crown ethers as a result of complexation with alkali metal ions.

De Silva and co-authors describe (e.g., Journal of the Chemical Society Perkin Transactions II 1992, 1559–1564, 1992) ion sensors in which the binding of ions suppresses an electron transfer between an ionophor and a fluorophor, thereby increasing fluorescence intensity. Aoki et al. (Journal of the Chemical Society Chemical Communications 1992, 730–732, 1992) show that in a system consisting of pyrene, calixarene and nitrobenzene fluorescence intensity is increased by ionic bonds. He et al. (Analytical Chemistry 65, 123–127, 1993) describe a sensor in which the fluorescence intensity of an ion-independent fluorophor is altered by the ion-dependent absorption of a ionophor.

In U.S. Pat. No. 5,154,890 a similar principle is disclosed. In that instance a potassium-selective fluoroionophor is immobilized in an ion-permeable polymer gel whose fluorescence intensity is selectively dependent on the potassium concentration of the sample.

All of the above devices are based on fluorescence intensity as an information carrier. Such devices have a major drawback, however, i.e., the measurement signal is affected in a hardly corrigible manner by unavoidable changes in the intensity of the light source, the passage of light through the optical system, the sensitivity of the detector, and, above all, the concentration of the indicator, which will reduce their practical usefulness. As a consequence, every single sensor element must be individually calibrated upon manufacture, and a second calibration must take place before its actual use (or, in the instance of prolonged test periods, periodic calibrations must be performed during usage).

The above disadvantages could be avoided by using fluorescence decay time instead of fluorescence intensity as measurement variable. Fluorescence decay time is an inherent property of the respective indicator and its molecular environment. It is independent of the thickness of the sensing layer, the concentration of the indicator substance, the intensity of the light source, the sensitivity of the detector, and the optical properties of the measuring system. For this reason, variations between individual sensor elements due to the manufacturing process do not produce different sensor characteristics, and a calibrating function determined for one element will be of relevance for all other elements, thus eliminating the necessity of individual calibration. Similarly, any changes in a sensor element due to ageing will not lead to a change in the sensor characteristic, so that no re-calibration will be needed before the actual measurement.

Bacon and Demas (U.S. Pat. No. 5,030,420) as well as Lippitsch et al. (Analytica Chimica Acta 205, 1–6, 1988) propose such a decay time sensor for oxygen measurement. Decay time sensors for pH (WO 92/10739), calcium (Lakowicz et al., Cell Calcium 13, 131–147, 1992), aluminium, gallium, and indium (Caroll et al., Analytical Chemistry 61, 1768–1772, 1989) have been described so far. As yet, no decay time sensors for alkali metal ions have been disclosed, however.

AT-PS 393 035 discloses a method for quantitative determination of a chemical parameter of a sample in which the indicator consists of two substances placed within close proximity of each other, i.e., a fluorophor and a chromophor. While the fluorophor does not respond to the parameter to be determined, the chromophor is subject to a change in its absorption spectrum. As there is a partial overlap between the emission spectrum of the fluorophor and the absorption spectrum of the chromophor, an energy transfer takes place between the two substances, and the fluorescence decay time of the fluorophor is decreased in dependence on the chemical parameter.

SUMMARY OF THE INVENTION

It is an object of the invention to propose luminescence-optical indicators based on decay time measurement for determining the activity of alkali metal ions, and sensor configurations comprising such indicators.

In the invention this is achieved by providing that the indicator have at least three components that are chemically bound to one another, i.e., a fluorophor, a functional group with which the luminescence decay time of the fluorophor can be influenced, and a ionophor selectively and reversibly binding the alkali metal ions to be measured, such that the effect of the functional group on the decay time of the fluorophor can be altered depending on the activity of the alkali metal ions.

The invention further provides that the absorption maximum of the fluorophor be in the wavelength range of 400–1,200 nm, and that the luminescence decay time of the fluorophor be greater than 10 ns.

To summarize, an indicator of the invention comprises at least one fluorophor, with an absorption preferably in the visible or near infrared range of the spectrum (400–1,200 nm) and a preferred fluorescence decay time of greater >10 ns, at least one functional group influencing the fluorescence decay time of the fluorophor by interaction with the latter, at least one ionophor forming a specific and reversible bond with a special type of alkali metal ions, thereby altering the interaction between functional group and fluorophor, and in this way making the fluorescence decay time of the fluorophor a function of the concentration of the respective alkali metal ion.

The three components are placed within close proximity of each other, either by being chemically linked to one another, or by being immobilized side by side in a suitable matrix.

Following are some examples of suitable fluorophors, functional groups and ionophors, and their respective properties that are essential for the invention.

Abbreviations used $l_a$ long-wave end of the absorption band
$t_f$ fluorescence decay time
$K_s$ bonding constant ionophor/cation
pKS decadic logarithm of $K_s$

| Examples of fluorophors | | |
|---|---|---|
| Substance | la (nm) | tf (ns) |
| 2-aminoanthracene | 480 | 31 |
| rubrene | 560 | 17 |
| decacyclene | 490 | 28 |
| ruthenium-bipyridyl | 550 | 545 |
| ruthenium-phenantroline | 447 | 950 |

Other possible fluorophors are polycyclic and heterocyclic aromatics and metal ion complexes with heterocyclic ligands, provided their fluorescence decay time can be influenced by functional groups.

| Examples of functional groups | |
|---|---|
| Substance | type of t-influence |
| nitro-, cyano- | electron acceptor |
| amino-, methoxy- | electron donor |
| viologene | electron acceptor |
| halides, pseudohalides | electron acceptor |

| Examples of ionophors | | |
|---|---|---|
| Substance | cation | pKS |
| calix(4)arene ester | $Na^+$ | 4.3 |
| | $K^+$ | 2.9 |
| 1,4-benzodioxin-23-crown-7-lariatether | $K^+$ | 3.0 |
| | $Na^+$ | <0.6 |
| 2,9-dibutyl-1,10-phenanthroline | $Li^+$ | ca.4.5 |
| | $Na^+$ | <2 |

Following is a description of possible indicators used for determining the $Na^+$-, $K^+$- and $Li^+$-activity of a sample. These examples only serve for the purpose of illustrating the invention, and do not restrict the subject of the invention in any way.

1. Indicator for measuring the activity of Na⁺ ions

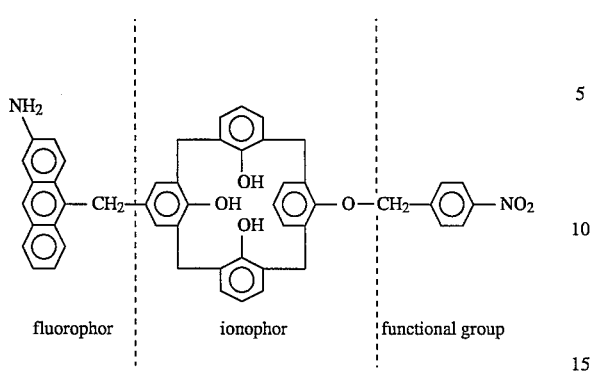

fluorophor | ionophor | functional group

In this example the fluorophor is 2-aminoanthracene, the functional group is nitrophenylmethyl, the ionophor is a calix(4)arene. If the ionophor has not bound a cation, the rings to which the functional group or the fluorophor are attached, may rotate freely. Due to the thermal motion the two components will frequently approach each other; as the nitro group has a quenching effect on the fluorophor, fluorescence decay time will be decreased. The ionophor has a high selectivity for the binding of Na⁺. If such an ion is attached the position of the rings is fixed by the interaction of the phenol oxygen atoms and the ion, no more quenching can take place, and the decay time approximately reaches the value of the unquenched fluorophor.

2. Indicators for measuring the activity of K⁺ ions (a)

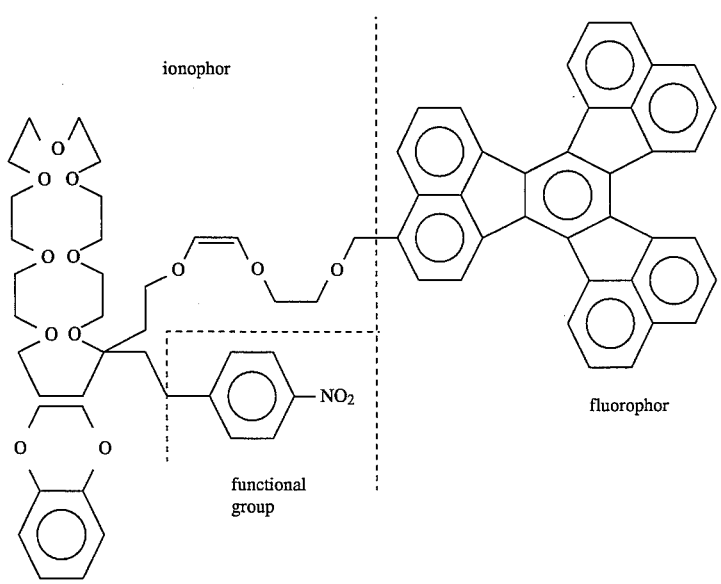

ionophor | functional group | fluorophor (b)

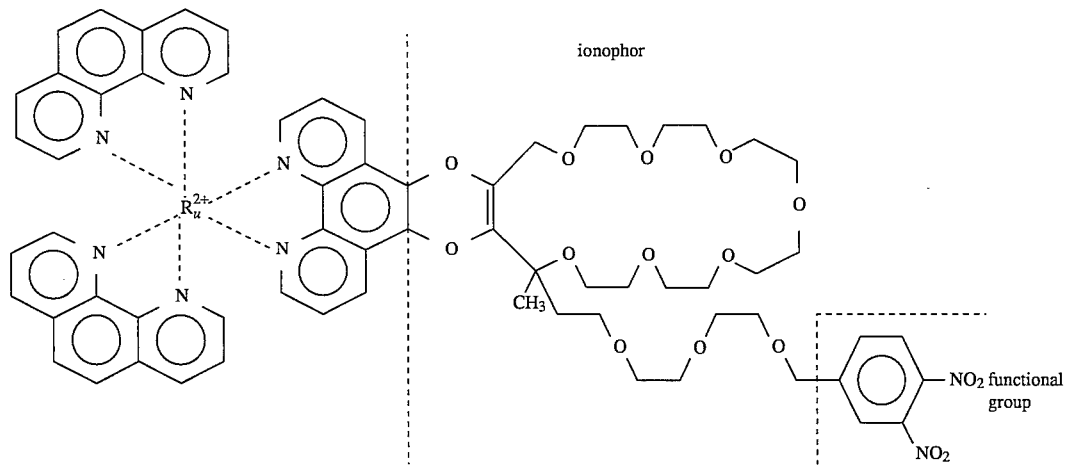

ionophor | NO₂ functional group

In example (a) the fluorophor is decacyclene, the functional group nitrophenylmethyl, the ionophor a benzodioxin-23-crown-7-lariatether. In example (b) tris-ruthenium-phenanthroline is used as fluorophor, dinitrobenzene as functional group, and a benzodioxin-23-crown-7-lariatether as ionophor. If the ionophor has not bound a cation, the lateral arm to which the functional group is linked, can move freely. Due to the thermal motion this group will frequently approach the fluorophor, thus quenching its fluorescence and reducing fluorescence decay time. The ionophor has a high selectivity for the binding of $K^+$. If such an ion is bound the position of the lateral arm is fixed by the interaction of the ester oxygen atoms and the ion, no more quenching can take place, and the decay time approximately reaches the value of the unquenched fluorophor.

cence decay time is independent of changes in the concentration of the indicator and of changes in the geometry of the light path (due to a swelling of the polymer matrix caused by physical-chemical properties of the sample). For this reason the measuring device is resistant to weak bleaching effects, indicator diffusion into the sample, and changes in the geometry of the light path. This immobilization variant is of special advantage if the device is used as a one-way measuring element.

Another possibility of incorporating the indicators of the invention into the polymer matrix is to chemically immobilize them by covalent bonding. This is of special advantage if the device is in contact with the sample for a prolonged period of time (continuous measurements, long-term measurements), or if the sample is to be protected from 3. Indicator for measuring the activity of $Li^+$ ions

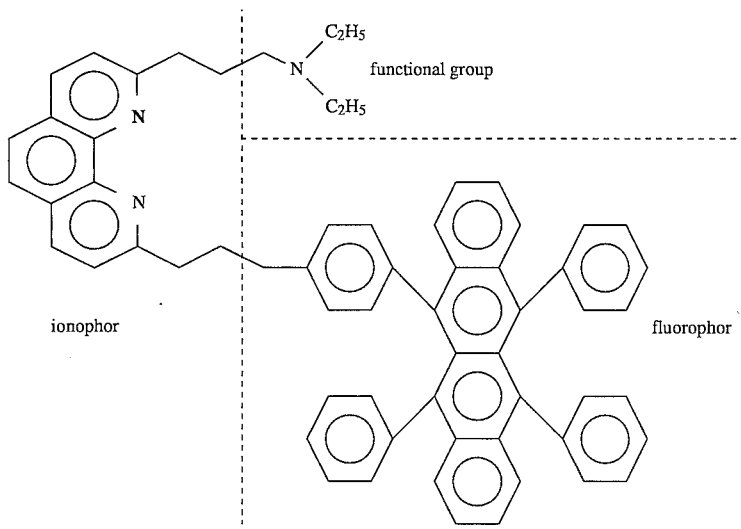

The fluorophor in this instance is rubrene, the functional group diethylamine, the ionophor dibutylphenanthroline. If the ionophor has not bound a cation, the butyl groups to which the functional groups are attached, can move freely. Due to the thermal motion the two components will frequently approach the fluorophor, the amino group acting as a fluorescence quencher and reducing fluorescence decay time. The ionophor has a high selectivity for the binding of $Li^+$. If such an ion is bound the position of the amino group is fixed by the interaction with the ion, and the positive charge of the ion will bind the free ion pairs of the nitrogen atoms. No more quenching can take place, and the decay time approximately reaches the value of the unquenched fluorophor.

In a sensor configuration using the indicator described in the invention it is provided that the indicator be incorporated in a hydrophilic, ion-permeable matrix on a carrier substrate transparent to the excitation and measurement radiation, the indicator preferably being physically dissolved in the hydrophilic, ion-permeable matrix. It would also be possible, however, to incorporate the indicator in the matrix by electrostatic or covalent bonding.

A low-cost method of immobilizing alkali metal ion-selective fluorescent indicators in an ion-permeable, hydrophilic polymer matrix is to physically dissolve the indicators in this matrix. Unlike the measurement of fluorescence intensity or light absorption, the measurement of fluoresbeing contaminated by the indicator substance (in-vivo measurements). For chemical immobilization of the indicators a number of methods may be employed that have already been described in the relevant literature, for example, by E. Koller and O. S. Wolfbeis in "Fiber Optic Chemical Sensors and Biosensors", vol. 1, chapter 7, O. S. Wolfbeis (ed.), CRC Press, Boca Raton 1991.

BRIEF DESCRIPTION OF THE FIGURE

The accompanying FIGURE schematically depicts a portion of a sensor containing an indicator according to the invention and its use in conjunction with a excitation device, a measuring unit and an evaluation unit for determining the activity of alkali metal ions in a sample solution.

DETAILED DESCRIPTION OF THE PREFERRED EMBODIMENT

The enclosed FIGURE presents a typical sensor configuration using the indicator of the invention. The luminescence-optical indicator I for determining the activity of alkali metal ions (e.g., $Na^+$ ions) in a sample solution P is provided in a hydrophilic, ion-permeable matrix M, where it is (preferably) physically dissolved. The ion-permeable matrix M forms a layer on a substrate or carrier T transparent to the excitation and measurement radiation. Further included are units A for excitation and M' for measurement, which are in optical contact with the indicator I. The signals of the measuring unit M' are transmitted to an evaluation unit P for determination of the decay time, or rather, its change, and the ion activity connected therewith.

The sensor S, which comprises the carrier T, the matrix M, and the indicator I dissolved therein, could also be dry-stored until its (one-time) use, in which instance the polymer hydrophilic matrix M will swell only upon contact with the aqueous sample P. Hydrophilic polymer supporting materials which swell upon contact with aqueous samples within a few seconds are known in the art. A major advantage of the invention is that no calibration of the measuring system by means of a calibrating liquid is required prior to the actual measurement process. Unlike in conventional optical measuring systems for alkali metal ions, the measurement signal is independent of fluctuations in the intensity of the light source, sensitivity of the detector and concentration of the indicator. The characteristic of the measuring device, which is dependent on the measurement variable, depends only on which types of indicator and polymer carrier material are used.

Suitable materials for the ion-permeable polymer matrix M include hydrogels, polyvinyl alcohols, polyglycols, polysaccharides, polyacrylates, polyacrylamides, polyimines, polyurethanes and their derivatives. Suitable carriers T of the matrix M are lightguides, glass slides or plastic foil, such as polyester, polycarbonate, etc.

As is known in the art, there are two essentially different ways of measuring fluorescence decay time, i.e., either by excitation with short light pulses and time-resolved recording of the generated fluorescence, or by excitation with high-frequency-modulated light and measurement of the phase shift between the modulation of the excitation light and the fluorescent light, or the modulation depth of the latter. In the sensor configuration of the invention either method may be used.

In an embodiment of the invention the indicator I is immobilized in a polymer matrix, For example, and contacted with the sample solution P. Fluorescence is excited with the use of a short-time light source, such as a coaxial flash lamp, a pulsed laser, or a pulsed LED. By means of a cut-off filter F, the fluorescent light is separated from the excitation light, and a high-speed photodetector (photomultiplier, pin-photodiode, avalanche photodiode) is used for fluorescence detection. Decay time is measured with suitable electronic means. Via a calibrating function which is stored only once, ionic concentrations or activities may be calculated from the measured decay times.

If phase-fluorometry is used, the light source (lamp, laser, LED) is high-frequency-modulated, fluorescence is separated spectrally and detected by means of a fast photodetector. In that instance the phase shift between the modulation of the excitation light and that of the fluorescent light is a function of fluorescence decay time, and therefore of ionic concentration.

We claim:

1. A luminescence-optical indicator for determining the activity of alkali metal ions in a sample solution through at least indirect contact with said sample solution, wherein said luminescence-optical indicator comprises at least three components: a fluorophor having a defined luminescence decay time, a functional group with which said luminescence decay time of said fluorophor can be influenced, and a ionophor selectively and reversibly binding said alkali metal ions to be measured such that said functional group alters said decay time of said fluorophor depending on the activity of said alkali metal ions, said fluorophor being chemically bound to said ionophor and said ionophor being chemically bound to said functional group.

2. An indicator according to claim 1, wherein an absorption maximum of said fluorophor is in the wavelength range of 400–1,200 nm.

3. An indicator according to claim 1, wherein said luminescence decay time of said fluorophor is greater than 10 ns.

4. An indicator according to claim 1, wherein said fluorophor is selected from the group consisting of 2-aminoanthracene, rubrene, decacyclene, trisruthenium-bipyridyl, and tris-ruthenium-phenantroline; wherein said functional group is selected from the group consisting of nitro-, cyano-, amino-, methoxy-groups, viologenes, halides, and pseudohalides; and wherein said ionophor is selected from the group consisting of calix(4)arene esters, 1,4-benzo-dioxin-23-crown-7-lariatether, and 2,9-dibutyl-1,10-phenanthroline.

5. An indicator according to claim 1, wherein said fluorophor is selected from the group consisting of polycyclic and heterocyclic aromatics and metal ion complexes with heterocyclic ligands, whose fluorescence decay time is influenced by said functional groups.

6. An indicator according to claim 1, for determining the activity of $Na^+$ ions of a sample solution wherein said fluorophor is 2-aminoanthracene, said functional group is nitrophenylmethyl, and said ionophor is a calix(4)arene.

7. An indicator according to claim 1, for determining the activity of $K^+$ ions of a sample solution, wherein said fluorophor is decacyclene, said functional group is nitrophenylmethyl, and said ionophor is a benzodioxin-23-crown-7-lariatether.

8. An indicator according to claim 1, for determining the activity of $K^+$ ions of a sample solution, wherein said fluorophor is tris-ruthenium-phenanthroline, said functional group is dinitrobenzene, and said ionophor is a benzodioxin-23-crown-7-lariatether.

9. An indicator according to claim 1, for determining the activity of the $Li^+$ ions of a sample solution, wherein said fluorophor is rubrene, said functional group is diethylamine, and said ionophor is dibutylphenanthroline.

10. A sensor comprising a luminescence-optical indicator for determining the activity of alkali metal ions in a sample solution through at least indirect contact with said sample solution and said luminescence-optical indicator is in optical contact with an excitation and measuring unit, wherein said luminescence-optical indicator has at least three components: a fluorophor having a defined luminescence decay time, a functional group with which said luminescence decay time of said fluorophor can be influenced, and a ionophor selectively and reversibly binding said alkali metal ions to be measured, such that said functional group alters said decay time of said fluorophor depending on the activity of said alkali metal ions, said fluorophor being chemically bound to said ionophor and said ionophor being chemically bound to said functional group, and wherein said luminescence-optical indicator is incorporated in a hydrophilic, ion-permeable matrix on a carrier substrate transparent to excitation and measurement radiation.

11. A sensor according to claim 10, wherein said luminescence-optical indicator is physically dissolved in said hydrophilic, ion-permeable matrix.

12. A sensor according to claim 10, wherein said luminescence-optical indicator is incorporated in said hydrophilic, ion-permeable matrix by electrostatic bonding.

13. A sensor according to claim 10, wherein said luminescence-optical indicator is incorporated in said hydrophilic, ion-permeable matrix by covalent bounding.

* * * * *